(12) United States Patent
Brojek

(10) Patent No.: US 11,826,697 B2
(45) Date of Patent: Nov. 28, 2023

(54) METHOD OF PREPARING THE CRYOGENIC AIR USED FOR CRYOTHERAPY

(71) Applicant: METRUM CRYOFLEX SP.Z.O.O. SPOLKA KOMANDYTOWA, Stare Babice (PL)

(72) Inventor: Wieslaw Brojek, Stare Babice (PL)

(73) Assignee: METRUM CRYOFLEX S.P. Z O.O., Spółka Komandytowa, Stare Babice (PL)

( * ) Notice: Subject to any disclaimer, the term of this patent is extended or adjusted under 35 U.S.C. 154(b) by 522 days.

(21) Appl. No.: 17/062,505

(22) Filed: Oct. 2, 2020

(65) Prior Publication Data

US 2021/0156605 A1 May 27, 2021

Related U.S. Application Data

(60) Provisional application No. 62/909,715, filed on Oct. 2, 2019.

(51) Int. Cl.
*A61F 7/00* (2006.01)
*B01D 53/26* (2006.01)

(52) U.S. Cl.
CPC .......... *B01D 53/265* (2013.01); *A61F 7/0053* (2013.01); *A61F 2007/0063* (2013.01); *A61F 2007/0064* (2013.01)

(58) Field of Classification Search
CPC .......... A61B 18/0218; A61F 2007/006; A61F 2007/0064; A61F 7/0053; A61F 7/0085
See application file for complete search history.

(56) References Cited

U.S. PATENT DOCUMENTS 8,162,930 B2 * 4/2012 Brojek .................. A61F 7/0053
606/22

* cited by examiner

Primary Examiner — Tigist S Demie
(74) Attorney, Agent, or Firm — Andrzej Malarz, Esq.

(57) ABSTRACT

A method of preparing cryogenic air for use in cryotherapy procedures, characterized in that liquid nitrogen (1) is fed from a cryogenic nitrogen tank (2) via a cryogenic duct (3) to at least one exchanger (4), wherein at the same time a breathing mixture (6), containing oxygen in a concentration of 17% to 100%, is fed, via an oxygen duct (7), from a breathing mixture (6) source (5), through the filter (8), to at least one exchanger (4), then in at least one exchanger (4), by means of a heat exchange between the breathing mixture (6) and liquid nitrogen (1), the breathing mixture (6) is cooled to the set temperature of minus 80° C. to minus 160° C., and then the cooled breathing mixture (6) is fed from at least one exchanger (4), via an upper pipe (9).

7 Claims, 6 Drawing Sheets

METHOD OF PREPARING THE CRYOGENIC AIR USED FOR CRYOTHERAPY

CROSS REFERENCE TO RELATED APPLICATIONS

This application claims the priority of U.S. Provisional Patent Application No.: 62/909,715, filed Oct. 2, 2019. The contents of U.S. Provisional Patent Application 62/909,715 are hereby incorporated by reference for all purposes.

FIELD OF THE INVENTION

The disclosure relates to a method of preparing cryogenic air for use in cryotherapy procedures.

BACKGROUND

The use of cryotherapy procedures employing the stimulus effect of low temperatures in the range of minus 80° C. to minus 160° C. acting over a short period of time is aimed at causing physiological and systematic reaction to cold stimuli. Such action supports the treatment of diseases particularly associated with human mobility limitations, such as inflammatory and degenerative joint diseases, rheumatoid arthritis (RA), ankylosing spondylitis (AS), shoulder impingement syndrome (SIS), spinal pain syndromes (surgically and conservatively treated), and, in addition, osteoporosis, fibromyalgia, connective tissue diseases, migraines and others.

Cryotherapy procedures allow for, among others, analgesic, anti-edematous, and anti-inflammatory effects, muscle tone reduction, strengthening and stimulation of the immune system, improvement of peristalsis peripheral vessels, cleansing and regeneration of the skin-anti-cellulite treatment, improvement of regeneration and healing processes, improvement of mood and increase of body efficiency.

In medical technology, devices for cryotherapy procedures are known, which consist of a low-temperature chamber, a system supplying such chamber with gas at cryogenic temperature, and systems controlling the operation of these devices.

A device for obtaining air at cryogenic temperature, intended for supplying a cryotherapy treatment chamber, comprising an air compressor, a dryer for removing steam from the compressed air, a heat exchanger and a container of liquefied gas is disclosed in German patent specification DE 3213919. The device is equipped with measurement, control and safety elements. Parts of the device containing agents at cryogenic temperature are provided with thermal insulation. The device requires a long start-up and preparation time.

A device is known, according to Polish patent specification PL 157168, which includes: an air compressor, a dryer for removing steam from the compressed air, a heat exchanger and a container for liquefied gas, preferably liquid nitrogen. All these basic components of the device are connected to each other by tubing. The liquefied gas from the tank flows to the heat exchanger, where it cools the air to the cryogenic temperature, air then flows through an insulated line to the low-temperature chamber. The whole device is equipped with measurement, control and safety elements, and parts of this device containing agents at cryogenic temperature are equipped with thermal insulation.

A method of preparing cryogenic air fed to the cryogenic chamber and a device for implementing such method described in Polish patent specification PL 190 389 is known. This method involves compressing, drying and cooling the air. This method is characterized by the fact that the air is compressed to 1 Mpa in the compressor, dried in the adsorber and directed to purge the cryogenic purifiers. Then the system is blown through and the air guiding valves are closed. The next step is to open the valves at the liquid nitrogen tank, allowing liquid nitrogen to flow from the tank intended for cooling the cryogenic purifier into which the air compressed in the compressor and purified in the adsorption dryer is directed. Simultaneously with cooling the cryogenic purifier, a second cryogenic purifier is also cooled. When the temperature of the air flowing from the cryogenic purifier to the cryochamber increases to about minus 100° C., the cryogenic purifier closes automatically and the air is sent to the second cryogenic purifier and then, after cooling and purifying, the air is sent to the cryochamber, while the air regenerates and cools in the cryogenic purifier. After the system operation is finished, it is regenerated with the valves open and the heaters turned on.

Furthermore, a method for preparing cryogenic air fed to the cryogenic chamber, described in patent specification PL 213499, according to the invention, is known, which consists in drying and cooling of the air. This method is characterized by the fact that the air is subjected to filtration, then it is dried in a rotary dryer and then compressed and passed through a evaporator of the antechamber of the cryogenic chamber where the air is initially cooled to a temperature of 0° C. to minus 60° C., then the air is passed through the evaporators of the cryogenic chamber where the air cools down to the set temperature of minus 100° C. to minus 160° C. The air is passed through two evaporators located in the cryogenic chamber. The air is compressed to a pressure of 0 to 40 millibars. The air is compressed to a variable pressure, whereby the air is compressed to a higher value with the antechamber or cabin door open, while the air is compressed to a lower value with the antechamber and cabin door closed. The same specification also discloses a device for the preparation of cryogenic air fed to the cryogenic chamber, which, according to the invention, is characterized in that it consists of a set of filters connected to a rotary dryer and the outlet of the rotary dryer is connected to an inlet of a turbine with flow control, while the turbine outlet is connected, with a duct, to an evaporator of the cryogenic chamber antechamber, and the antechamber evaporator outlet duct is connected to an inlet of the cryogenic chamber evaporator while the evaporator outlet comprises an inlet of the cryogenic chamber. Each evaporator is made of two sets of tubes, air and nitrogen, located next to each other. The air tubes are arranged between the nitrogen tubes and connected to them by cooling lamellas.

The disadvantages of the solutions know in the art are the losses of liquid nitrogen that occur when it is fed during cryotherapy.

SUMMARY

The solution according to the invention increases the efficiency of using the nitrogen agent by eliminating losses, which results in a significant reduction of the cost of procedures borne by the patient.

However, in the cryosaunas that are known in the art, cryotherapy does not cover the entire human body, and thus there is no cryostimulation in the area of the head, upper arms, chest and back, i.e. in the areas where the largest number (estimated at approx. 40% of approx. 120,000) of cold receptors is located. The existing cryosaunas do not have the functionality of applying a cold stream into the abovementioned areas because administering a non-breathable gas mixture around the head results in a life-threatening condition.

The solution according to the invention completely eliminates these disadvantages by providing cryostimulation of the entire body of the patient, i.e. including the area of the head, upper arms, chest and upper back.

Essential for the invention is the method of preparing cryogenic air for use in cryotherapy procedures, characterized in that liquid nitrogen is fed from a cryogenic nitrogen tank via a cryogenic duct to at least one exchanger, while at the same time a breathing mixture, containing oxygen in a concentration from 17% to 100%, is fed, via an oxygen duct, from a breathing mixture source, through the filter, to at least one exchanger, wherein in at least one exchanger, by means of a heat exchange between the breathing mixture and liquid nitrogen, the breathing mixture is cooled to the set temperature of minus 80° C. to minus 160° C., and then the cooled breathing mixture is fed from at least one exchanger, via an upper pipe, and applied onto a head and shoulder girdle of a human located in a cryochamber, while at the same time liquid/gaseous nitrogen is fed, via the lower duct, to a non-breathable part of the cryochamber.

Preferably, at least one exchanger is located in the cryochamber.

Preferably, liquid nitrogen is fed from the cryogenic nitrogen tank, through the cryogenic duct, to the dryer, while at the same time the breathing mixture, containing oxygen in a concentration from 17 to 100%, is fed from the breathing mixture source, through the filter, to the dryer, wherein within the dryer the breathing mixture is pre-cooled and dried, and then the mixture is fed through the oxygen duct to at least one exchanger.

Preferably, the cryogenic duct is additionally connected to the cryochamber and used to supply the liquid/gaseous nitrogen mixture to the non-breathable part of the cryochamber.

Preferably, the cooled breathing mixture is fed, via the upper duct, from at least one exchanger and applied, through the feeder, onto the shoulder girdle and the head of a human located in a cryosauna, while at the same time liquid/gaseous nitrogen is fed, via the lower duct, from at least one exchanger to the lower part of the cryosauna.

Preferably, the cryogenic duct is additionally connected to the cryosauna and used to supply the liquid/gaseous nitrogen to the non-breathable part of the cryosauna.

Preferably, at least one exchanger is located in the cryosauna.

The embodiment of the invention is presented in more detail in the drawing, in which the method of preparing cryogenic air for use in cryotherapy procedures is schematically shown.

DETAILED DESCRIPTION OF THE PREFERRED EMBODIMENTS

Figure 1:
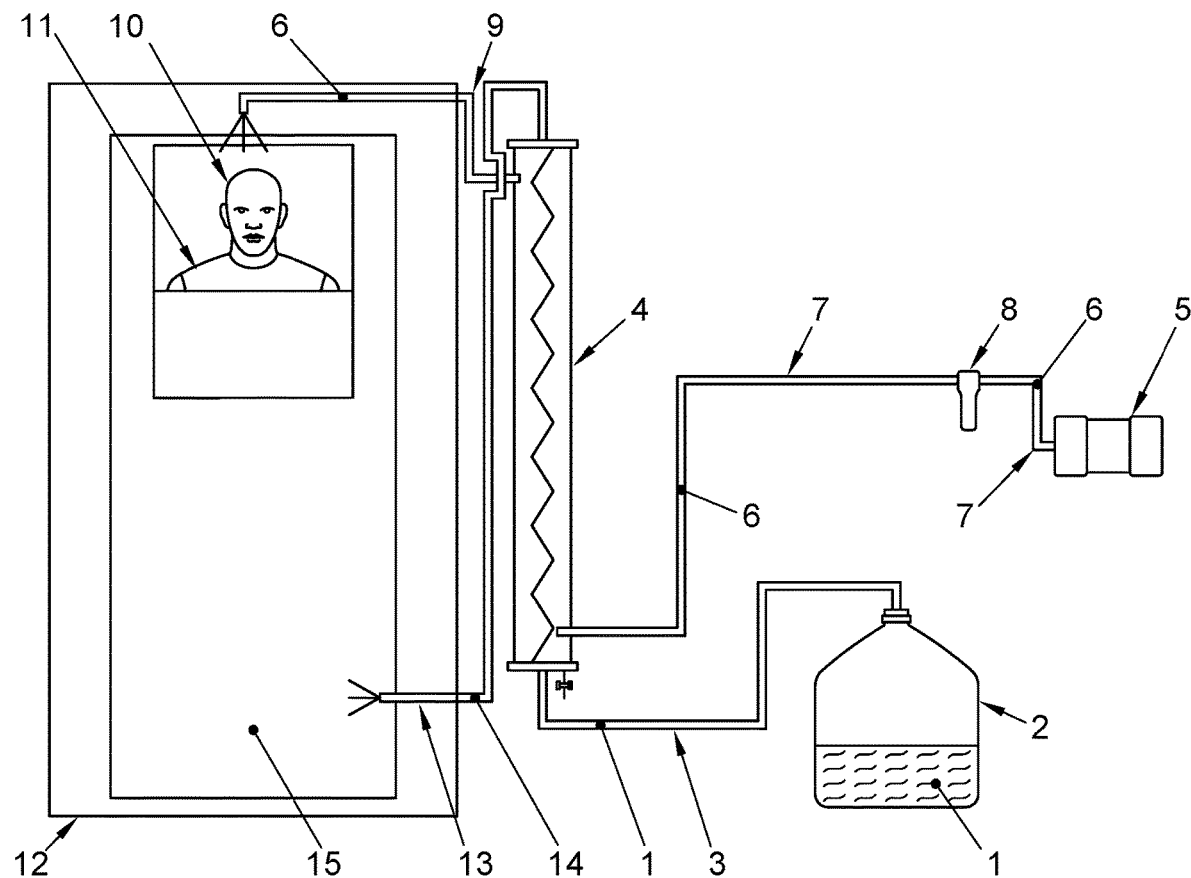
FIG. 1 shows a method of preparing cryogenic air for use in cryotherapy procedures.

FIG. 1 presents a method of preparing cryogenic air for use in cryotherapy procedures. Liquid nitrogen 1 is contained in a cryogenic nitrogen tank 2. Liquid nitrogen 1 is fed via a cryogenic duct 3, which connects the nitrogen tank 2 with an exchanger 4. A breathing mixture 6, having a high oxygen concentration, is fed from a source 5, via an oxygen duct 7, to an exchanger 4, through a filter 8. In the exchanger 4, a heat exchange between the breathing mixture 6 and liquid nitrogen 1 takes place and thus the breathing mixture 6 cools down to the set temperature of minus 160° C. Then, the cooled breathing mixture 6 is fed from the exchanger 4 via an upper duct 9, which connects the exchanger 4 to a cryochamber 12, onto the head 10 and shoulder girdle 11 of a human located in the cryochamber 12. At the same time, liquid/gaseous nitrogen 14 is fed via a bottom duct 13, which also connects the exchanger 4 to the cryochamber 12, to a non-breathable part 15 of the cryochamber 12.

Figure 2:
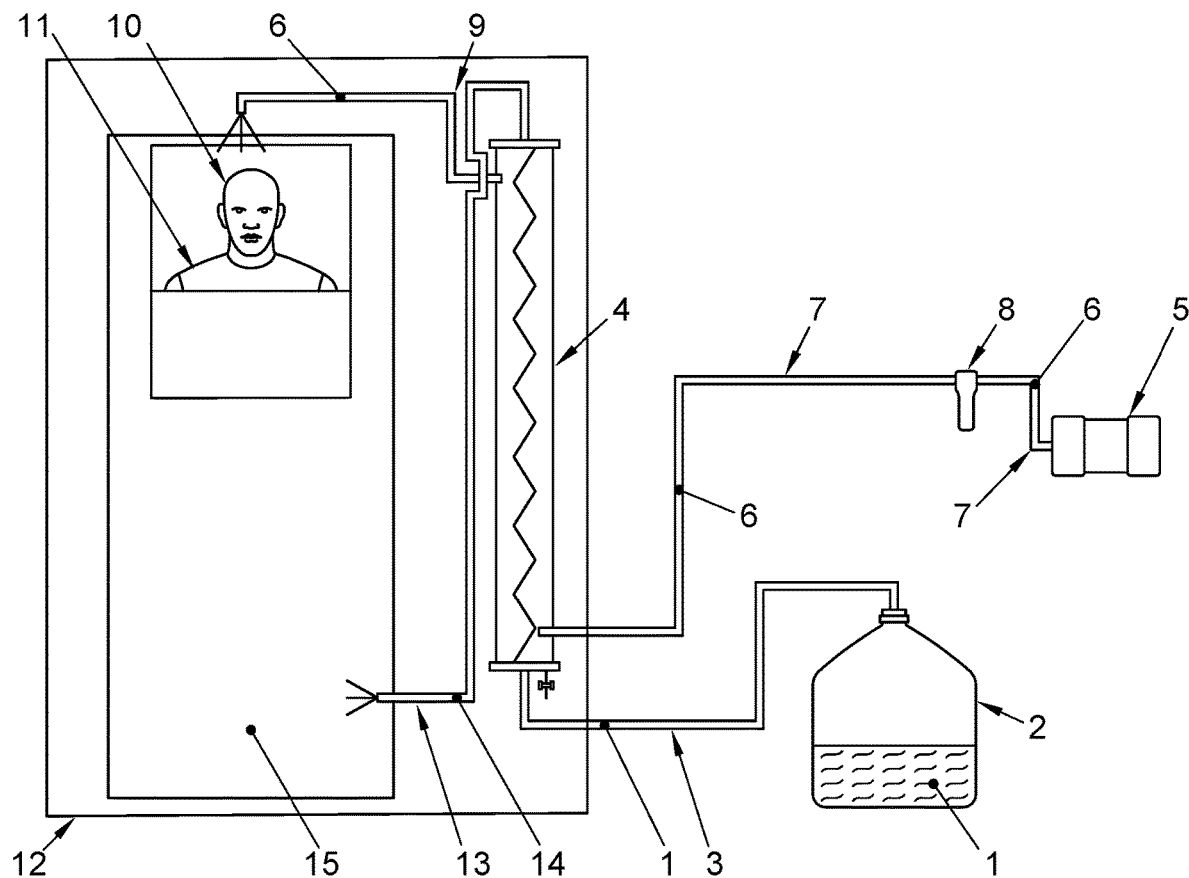
FIG. 2 shows a method of preparing cryogenic air for use in cryotherapy procedures similar to the method shown in FIG. 1.

FIG. 2 shows a method of preparing cryogenic air for use in cryotherapy procedures similar to the method shown in FIG. 1 above, the difference being that the exchanger 4 is located directly in the cryochamber 12.

Figure 3:
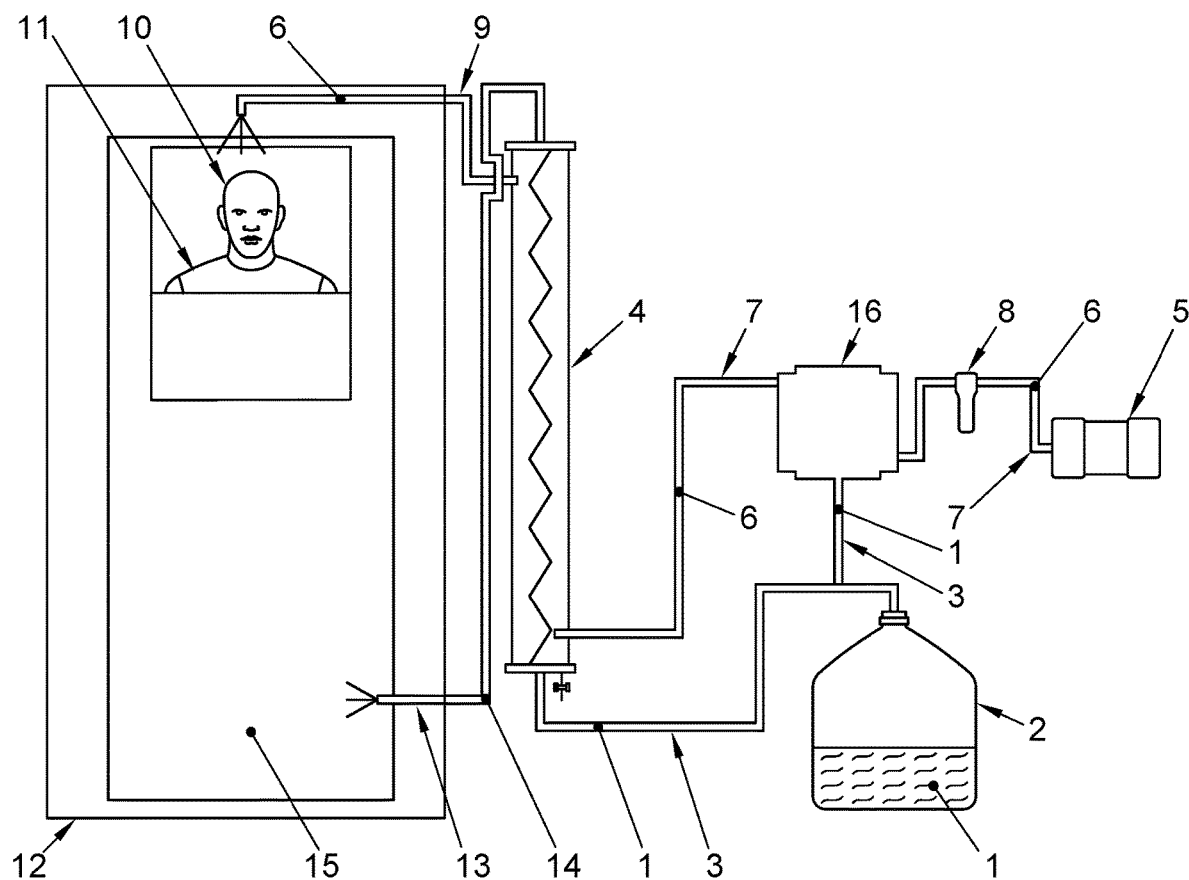
FIG. 3 shows a method of preparing cryogenic air for use in cryotherapy procedures, in which liquid nitrogen is fed from a cryogenic nitrogen tank via a cryogenic duct to a dryer.

FIG. 3 illustrates a method of preparing cryogenic air for use in cryotherapy procedures, in which liquid nitrogen 1 is fed from a cryogenic nitrogen tank 2 via a cryogenic duct 3 to a dryer 16. Meanwhile, a breathing mixture 6 having a high oxygen concentration is fed from a source 5 to the dryer 16, through a filter 8. In the dryer 16, the breathing mixture 6 is pre-cooled and dried, and then the mixture is fed to an exchanger 4 via an oxygen duct 7. In the exchanger 4, a heat exchange between the breathing mixture 6 and liquid nitrogen 1 takes place and thus the breathing mixture 6 cools down to the set temperature of minus 160° C. Then, the cooled breathing mixture 6 is fed from the exchanger 4 via an upper duct 9, which connects the exchanger 4 to a cryochamber 12, onto the head 10 and shoulder girdle 11 of a human located in the cryochamber 12. At the same time, liquid/gaseous nitrogen 14 is fed via a bottom duct 13, which also connects the exchanger 4 to the cryochamber 12, to a non-breathable part 15 of the cryochamber 12.

Figure 4:
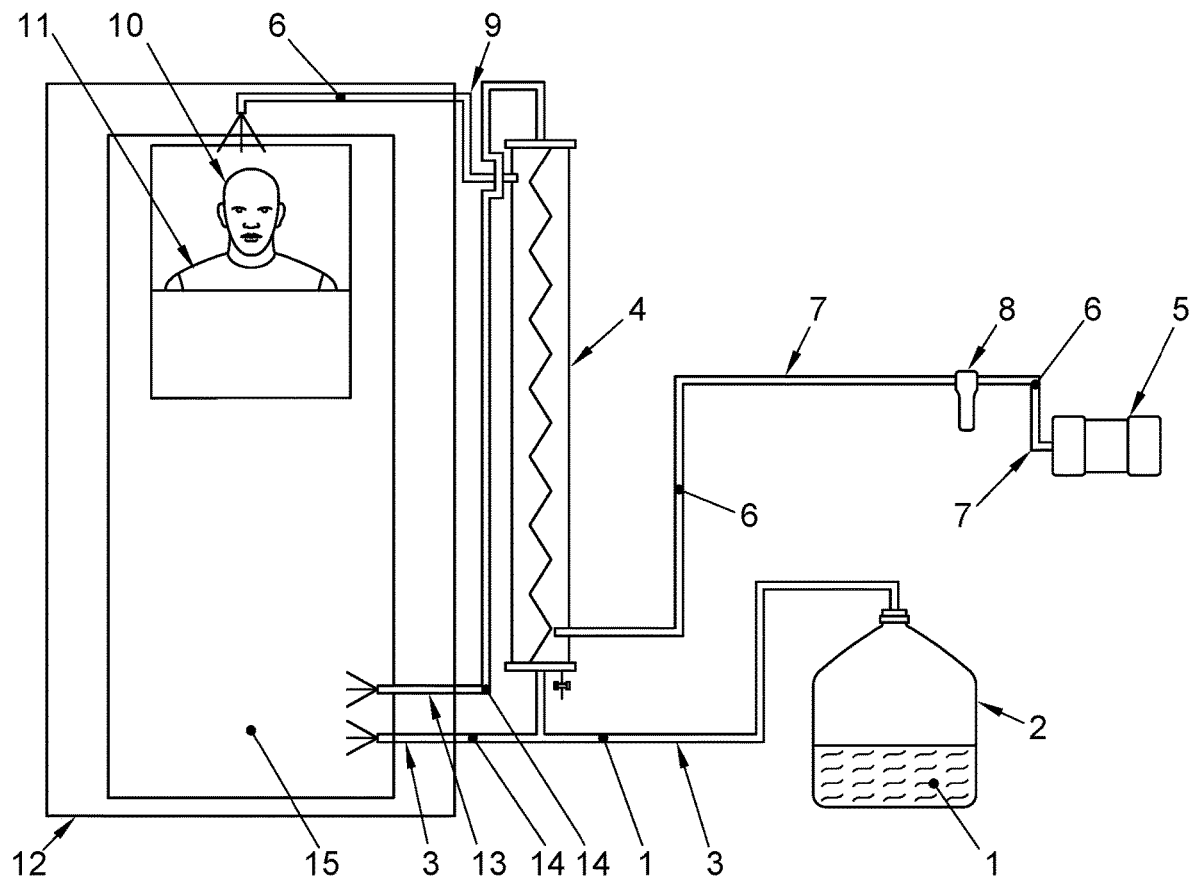
FIG. 4 shows a method of preparing cryogenic air for use in cryotherapy procedures, where a cryogenic nitrogen tank contains liquid nitrogen.

FIG. 4 discloses a method of preparing cryogenic air for use in cryotherapy procedures, where a cryogenic nitrogen tank 2 contains liquid nitrogen 1. Liquid nitrogen 1 is fed via a cryogenic duct 3, which connects the nitrogen tank 2 with an exchanger 4. A breathing mixture 6, having a high oxygen concentration, is fed from a source 5, via an oxygen duct 7, to an exchanger 4, through a filter 8. In the exchanger 4, a heat exchange between the breathing mixture 6 and liquid nitrogen 1 takes place and thus the breathing mixture 6 cools down to the set temperature of minus 160° C. Then, the cooled breathing mixture 6 is fed from the exchanger 4 via an upper duct 9, which connects the exchanger 4 to a cryochamber 12, onto the head 10 and shoulder girdle 11 of a human located in the cryochamber 12. At the same time, liquid/gaseous nitrogen 14 is fed via a bottom duct 13, which also connects the exchanger 4 to the cryochamber 12, to a non-breathable part 15 of the cryochamber 12. In addition, the cryogenic duct 3 is additionally connected to the cryochamber 12 and used to supply the liquid/gaseous nitrogen mixture 14 to the non-breathable part 15 of the cryochamber 12.

Figure 5:
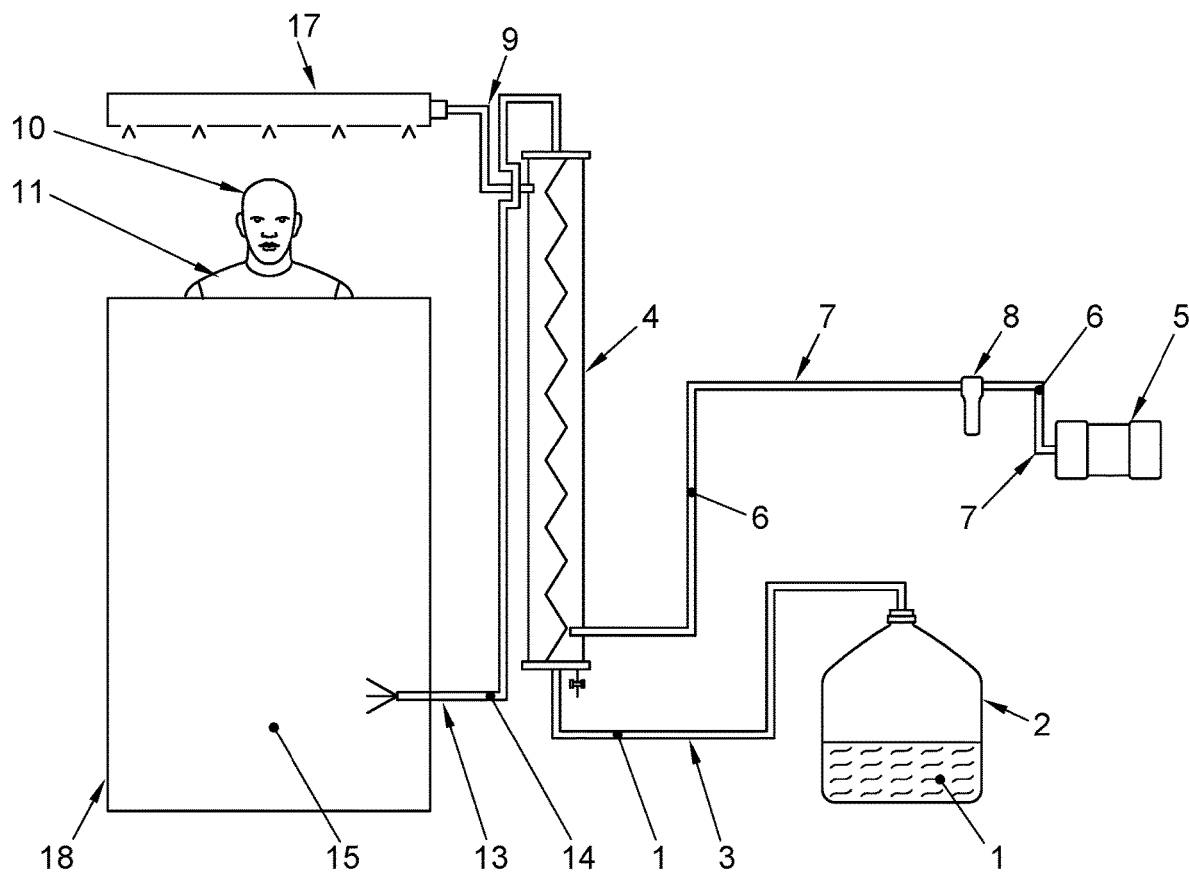
FIG. 5 shows a method of preparing cryogenic air for use in cryotherapy procedures performed in a cryosauna.

FIG. 5 illustrates a method of preparing cryogenic air for use in cryotherapy procedures performed in a cryosauna 18. Liquid nitrogen 1 contained in a nitrogen tank 2 is fed through a cryogenic duct 3 to an exchanger 4. Meanwhile, a breathing mixture 6 having a high oxygen concentration is fed, via an oxygen duct 7, from a source 5 to the exchanger 4, through a filter 8. In the exchanger 4, a heat exchange between the breathing mixture 6 and liquid nitrogen 1 takes place and thus the breathing mixture 6 cools down to the set temperature of minus 160° C. Then, the cooled breathing mixture 6 is fed from the exchanger 4 via an upper duct 9, which connects the exchanger 4 to a feeder 17, and applied through the feeder 17 onto the shoulder girdle 11 and head 10 of a human located in the cryosauna 18. At the same time liquid/gaseous nitrogen 14 is fed, via a lower duct 13, from the exchanger 4 to the lower part of the cryosauna 18.

Figure 6:
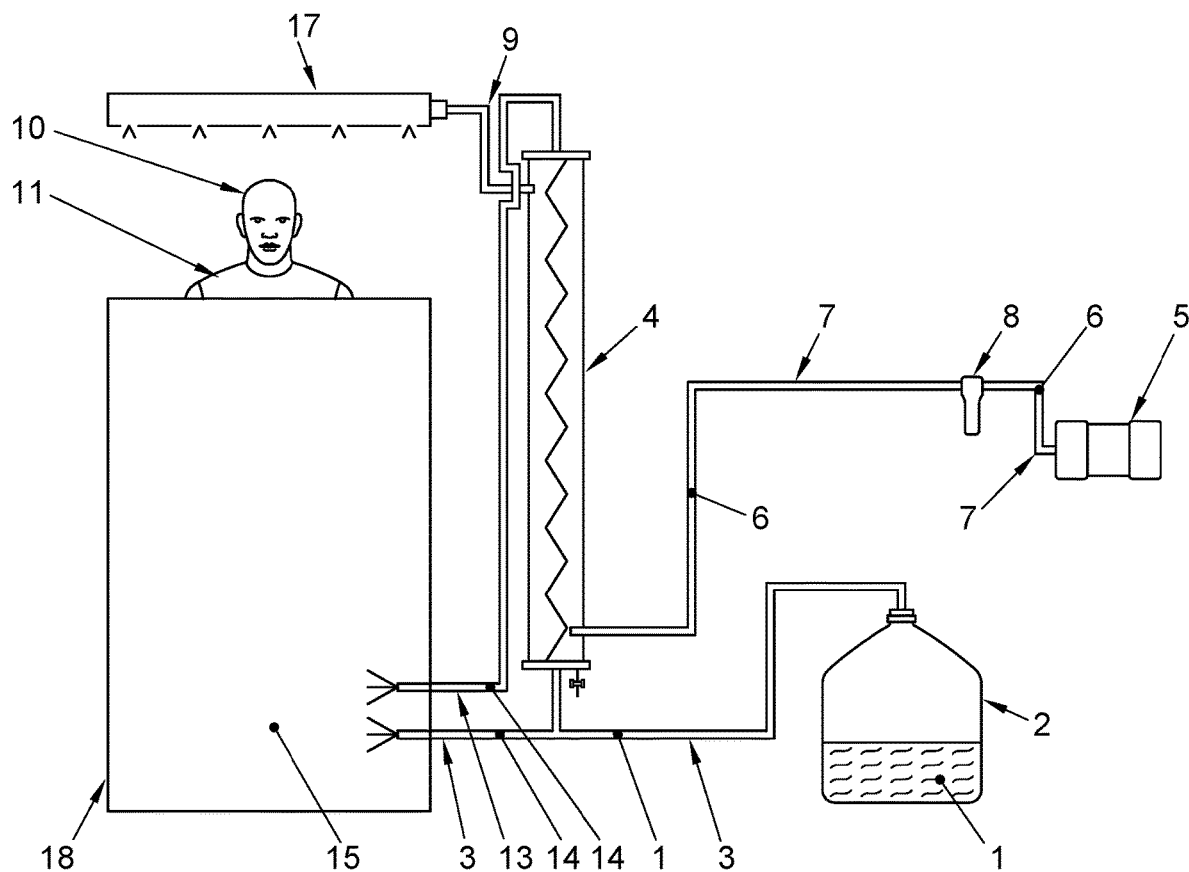
FIG. 6 shows a method of preparing cryogenic air for use in cryotherapy procedures performed in a cryosauna.

FIG. 6 presents a method of preparing cryogenic air for use in cryotherapy procedures performed in a cryosauna 18. This figure shows an additional connection of a cryogenic duct 3 to the cryosauna 18. The cryogenic duct 3 is used to supply the liquid/gaseous nitrogen 14 to the non-breathable part 15 of the cryosauna 18. In this figure, as in FIG. 5, the cooled breathing mixture 6 is fed from the exchanger 4 via an upper duct 9, which connects the exchanger 4 to a feeder 17, and applied through the feeder 17 onto the shoulder girdle 11 and head 10 of a human located in the cryosauna 18. At the same time liquid/gaseous nitrogen 14 is fed, via a lower duct 13, from the exchanger 4 to the lower part of the cryosauna 18.

It is also possible, but not shown in the figure, that the exchanger 4 is located directly in cryosauna 18.

In the embodiments presented above, there is one exchanger, however, it is possible to use more exchangers that operate alternately. This way, high efficiency of the heat exchange is maintained by eliminating the phenomenon of frosting which causes significant thermal resistance. This allows for continuous and effective operation of cryochambers and cryosaunas.

The implementation of the method according to the invention allows for a significant, practically complete, elimination of liquid nitrogen losses, which is used in the method of preparing cryogenic air for use in cryotherapy procedures performed in a cryochamber or cryosauna.

The implementation of the lower duct allows for the delivery of liquid/gaseous nitrogen to the non-breathable part of the cryochamber or the lower part of the cryosauna, thereby increasing the effectiveness of cryotherapy, reducing preparation time and reducing the costs of the procedure. An additional increase in the effectiveness of cryotherapy is achieved through the implementation of a cryogenic duct directly in a cryochamber or cryosauna, which is included in the embodiments, specifically in FIGS. 4 and 6. The presented additional connection of the cryogenic duct with the cryochamber or cryosauna significantly reduces the costs of the procedure due to the shortening of its duration.

The solution according to the invention allows both for development of a new product in the form of a completely new cryochamber or cryosauna and for the implementation of the method of preparing cryogenic air for use in cryotherapy procedures in relation to cryochambers or cryosaunas already available on the market.

The solution according to the invention may be used, among others, in health centers, spa facilities and sports clubs.

While the present invention has been described at some length and with some particularity with respect to the several described embodiments, it is not intended that is should be limited to any such particulars or embodiments or any particular embodiment, but it is to be construed with references to be appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

The invention claimed is:

1. A method of preparing cryogenic air for use in cryotherapy procedures, characterized in that liquid nitrogen (1) is fed from a cryogenic nitrogen tank (2) via a cryogenic duct (3) to at least one exchanger (4), wherein at the same time a breathing mixture (6), containing oxygen in a concentration of 17% to 100%, is fed, via an oxygen duct (7), from a breathing mixture (6) source (5), through a filter (8), to the at least one exchanger (4), then in at least one exchanger (4), by means of a heat exchange between the breathing mixture (6) and liquid nitrogen (1), the breathing mixture (6) is cooled to a set temperature of minus 80° C. to minus 160° C., and then the cooled breathing mixture (6) is fed from the at least one exchanger (4), via an upper pipe (9), and applied onto a head (10) and shoulder girdle (11) of a human located in a cryochamber (12), while at the same time liquid/gaseous nitrogen (14) is fed, via a lower duct (13), to a non-breathable part (15) of the cryochamber (12).

2. The method of preparing cryogenic air according to claim 1, characterized in that the at least one exchanger (4) is located in the cryochamber (12).

3. The method of preparing cryogenic air according to claim 1, characterized in that the liquid nitrogen (1) is fed from the cryogenic nitrogen tank (2) via the cryogenic duct (3) to a dryer (16), wherein at the same time the breathing mixture (6), containing oxygen in a concentration from 20 to 100%, is fed from the breathing mixture (6) source (5), through the filter (8), to the dryer (16), wherein within the dryer (16) the breathing mixture (6) is pre-cooled and dried, and then the mixture is fed through the oxygen duct (7) to the at least one exchanger (4).

4. The method of preparing cryogenic air according to claim 1 characterized in that the cryogenic duct (3) is additionally connected to the cryochamber (12) and used to supply the liquid/gaseous nitrogen mixture (14) to the non-breathable part (15) of the cryochamber (12).

5. The method of preparing cryogenic air according to claim 1, characterized in that the cooled breathing mixture (6) is fed, via the upper duct (9), from the at least one exchanger (4) and applied, through a feeder (17), onto the shoulder girdle (11) and the head (10) of a human located in a cryosauna (18), while at the same time liquid/gaseous nitrogen (14) is fed, via the lower duct (13), from the at least one exchanger (4) to the lower part of the cryosauna (18).

6. The method of preparing cryogenic air according to claim 4, characterized in that the cryogenic duct (3) is additionally connected to a cryosauna (18) and used to supply the liquid/gaseous nitrogen (14) to the non-breathable part (15) of the cryosauna (18).

7. The method of preparing cryogenic air according to claim 5, characterized in that the at least one exchanger (4) is located in the cryosauna (18).

\* \* \* \* \*